US006503570B2

(12) United States Patent
Matsuki et al.

(10) Patent No.: US 6,503,570 B2
(45) Date of Patent: Jan. 7, 2003

(54) CYCLOSILANE COMPOUND, AND SOLUTION COMPOSITION AND PROCESS FOR FORMING A SILICON FILM

(75) Inventors: Yasuo Matsuki, Tokyo (JP); Satoshi Ebata, Tokyo (JP)

(73) Assignee: JRS Corporation, Tokyo (JP)

( * ) Notice: Subject to any disclaimer, the term of this patent is extended or adjusted under 35 U.S.C. 154(b) by 0 days.

(21) Appl. No.: 09/802,918

(22) Filed: Mar. 12, 2001

(65) Prior Publication Data

US 2001/0021760 A1 Sep. 13, 2001

(30) Foreign Application Priority Data

Mar. 13, 2000 (JP) ........................... 2000-069313
Mar. 13, 2000 (JP) ........................... 2000-069314
Jun. 1, 2000 (JP) ........................... 2000-164102

(51) Int. Cl.$^7$ ................................. B05D 3/02
(52) U.S. Cl. ........................ 427/387; 423/347
(58) Field of Search .................. 556/430; 423/347; 427/387

(56) References Cited

U.S. PATENT DOCUMENTS

| 4,554,180 A | * | 11/1985 | Hirooka .................. 136/258 |
| 4,683,145 A | * | 7/1987 | Nishimura et al. ......... 136/258 |
| 4,820,788 A | * | 4/1989 | Zeigler .................... 430/323 |

FOREIGN PATENT DOCUMENTS

| GB | 2 077 710 | 12/1981 |
| JP | 60-242612 | 12/1985 |
| JP | 64-29661 | 1/1989 |
| JP | 4-334551 | 11/1992 |
| JP | 7-267621 | 10/1995 |
| JP | 9-237927 | 9/1997 |

OTHER PUBLICATIONS

Werner Kern, et al., J. Vac. Sci. Technol., vol. 14, No. 5, pp. 1082–1099, "Advances in Deposition Processes for Passivation Films", Sep./Oct. 1977.
W. E. Spear, et al., Solid State Communications, vol. 17, No. 9, pp. 1193–1196, "Substitutional Doping of Amorphous Silicon", 1975.
Patricia A. Bianconi, et al., J. Am. Chem. Soc., vol. 110, No. 7,pp. 2342–2344, "Poly(N–Hexylsilyne): Synthesis and Properties of the First Alkyl Silicon $[RSI]_n$ Network Polymer", 1988.
Kazuaki Furukawa, et al., Macromolecules, vol. 23, No. 14, pp. 3423–3426, "Optical Properties of Silicon Network Polymers", 1990.
Koichi Mikami, et al., J. Chem. Soc., Chem. Commun., pp. 1161–1163, "Anomalous Threo–Diastereoselectivity in Allylic Silane— or Stannane–Aldehyde Condensation Reactions: New Interpretation of the Antiperiplanar vs. Synclinal Problem on the Transition–State Conformations", 1990.
Tatsuya Shono, et al., J. Chem. Soc., Chem. Commun., pp. 896–897, "Electroreductive Synthesis of Polygermane and Germane–Silane Copolymer", 1992.
K. Sakamoto, et al., Macromolecules, vol. 23, No. 20, pp. 4494–4496, "Highly Ordered High Molecular Weight Alternating Polysilyene Copolymer Prepared by Anionic Polymerization of Masked Disilene[1]", 1990.
E. Hengge, et al., Z. anorg. allg. Chem., vol. 459, pp. 123–130, "Darstellung Und Charakterisierung Von Cyclohexasilan $SI_6H_{12}$", 1979.
Edwin Hengge, et al., Monatshefte für Chemie, vol. 106, pp. 503–512, "Darstellung Und Eigenschaften Von Cyclopentasilan", 1975.
Harald Stüger, et al., Z. anorg. allg. Chem. vol. 621, pp. 1515–1522, "Anorganische BI(Cyclopentasilanyle): Synthese Und Spektroskopische Charakterisierung", 1995.
Philip Boudjouk, et al., J. Chem. Soc., Chem. Commun., pp. 777–778, "The Synthesis of the First Spiropentasilane, Octamethylspiropentasilane", 1984.
Masato Suzuki, et al., vol. 27, No. 8, pp. 2360–2363, "Synthesis of Sequence–Ordered Polysilane by Anionic Ring–Opening Polymerizatin of Phenylnonamethylcyclopentasilane[1]", 1994.
Makoto Kumada, Journal of Organometallic Chemistry, vol. 100, pp. 127–138, "Some Recent Studies of the Skeletal Transformations of Organopolysilanes", 1975.
E. Hengge, et al., Journal of Organometallic Chemistry, vol. 212, pp. 155–161, "An Electrochemical Method for the Synthesis of Silicion–Silicon Bonds", 1981.

* cited by examiner

*Primary Examiner*—Robert Dawson
*Assistant Examiner*—Marc S Zimmer
(74) *Attorney, Agent, or Firm*—Oblon, Spivak, McClelland, Maier & Neustadt, P.C.

(57) ABSTRACT

Silylcyclopentasilane and a solution composition for forming a silicon film containing the same, which is used for forming a silicon film on the surface of a substrate. There is also disclosed spiro[4.4] nonasilane.

24 Claims, 7 Drawing Sheets

CYCLOSILANE COMPOUND, AND SOLUTION COMPOSITION AND PROCESS FOR FORMING A SILICON FILM

DETAILED DESCRIPTION OF THE INVENTION

The present invention relates to a novel cyclosilane compound, a solution composition for forming a silicon film and a process for forming a silicon film.

Heretofore, thermal chemical vapor deposition (CVD), plasma CVD and optical CVD which use monosilane gas or disilane gas have been used to form an amorphous silicon film or polysilicon film. Generally speaking, thermal CVD (J. Vac. Sci. Technology, vol. 14, pp. 1082, 1977) and plasma CVD (Solid State Com., Vol. 17, pp. 1193, 1975) have been widely used for the formation of a polysilicon film and an amorphous silicon film, respectively, and these films have been used for the production of solar cells and liquid crystal display elements having a thin film transistor.

However, in the respect of a process for forming a silicon film in accordance with these CVD methods, further improvement on the following points has been awaited. (1) Since a gas-phase reaction is used, silicon particles generated in a gas phase contaminate an apparatus and form foreign matter, thereby reducing production yield. (2) Since raw materials are gaseous, it is difficult to obtain a uniformly thick film on a substrate having an uneven surface. (3) Productivity is low due to a low film formation speed. (4) A complex and expensive high-frequency generator and vacuum apparatus are needed for plasma CVD.

In the respect of raw materials, since gaseous silicon hydride which has high reactivity and toxicity is used, it is difficult to handle it and an airtight vacuum apparatus is required. This apparatus is bulky and expensive and a vacuum or plasma system consumes a huge amount of energy, thereby boosting the costs of a product.

A method of coating liquid silicon hydride without using a vacuum system has recently been proposed. JP-A 1-29661 (the term "JP-A" as used herein means an "unexamined published Japanese patent application") discloses a process for forming a silicon-based thin film by liquefying a gaseous raw material on a cooled substrate, adsorbing it to the substrate and reacting it with chemically active atomic hydrogen. However, this process involves such problems that a complex apparatus is required and that it is difficult to control the thickness of a film because silicon hydride as a raw material is vaporized and cooled successively.

JP-A 7-267621 discloses a process for coating a substrate with low-molecular weight liquid silicon hydride. This process has such problems that it is difficult to handle silicon hydride as the system is instable and that it is difficult to obtain a uniform film thickness when it is applied to a large-area substrate because silicon hydride is liquid.

Meanwhile, English Patent GB-2077710A reports an example of solid silicon hydride polymer but a coating film thereof cannot be formed because it is insoluble in a solvent.

Further, JP-A 9-237927 discloses a process for forming a silicon film by coating a substrate with a polysilane solution and thermally decomposing polysilane to liberate a silicon film in order to produce a solar cell. However, it is difficult to obtain an amorphous or polycrystal silicon film having excellent electrical properties from a silicon compound containing carbon because thermal decomposition or optical decomposition by exposure to ultraviolet radiation causes a large amount of carbon to remain in the film as an impurity.

Further, JP-A 60-242612 discloses a process for forming a silicon deposition film by thermal CVD, the process comprising forming a gaseous atmosphere of a cyclic silane compound represented by the following formula and a halogen compound in a deposition chamber where a substrate is placed and providing heat energy to these compounds to form a deposition film containing silicon atoms on the substrate.

(where n is 3, 4 or 5, R is H or $SiH_3$).

The above publication enumerates compounds represented by five chemical formulas as the cyclic silane compound represented by the above formula. However, it is silent about identification data on these cyclic compounds and a production process therefor. Polysilanes can be generally produced from monomers having a structural unit by the following methods, for example: (a) one in which a halosilane is dehalogenated and polycondensed in the presence of an alkali metal equivalent in weight to the halogen atom (so-called Kipping method, J. Am. Chem. Soc., vol. 110, pp. 2342, (1988), Macromolecules, vol. 23, pp. 3423, (1990)); (b) one in which a halosilane is dehalogenated and polycondensed by electrode reduction (J. Chem, Soc., Chem, Commun., pp. 1161, (1990), J. Chem. Soc., Chem. Commun., pp. 896, (1992); (c) one in which a hydrosilane is dehydrogenated and polycondensed in the presence of a metal catalyst (JP-A 4-334551); (d) one in which a disilane crosslinked by biphenyl is anionically polymerized (Macromolecules, vol. 23, pp. 4494, (1990)); and (e) one in which a cyclic silicon compound substituted by a phenyl group or alkyl group is synthesized by one of the above methods and induced into a hydro-substituted material or halogen-substituted material by a known method (for example, Z. Anorg. Allg. Chem., vol. 459, pp. 123, (1979)). These cyclosilane halide compounds may be synthesized by known methods (for example, Mh. Chem. vol. 106, pp. 503, (1975)), (Z. Anorg. Allg. Chem. vol. 621, pp. 1517, (1995)), (J. Chem. Soc., Chem. Commun., pp. 777, (1984)) As described above, a polysilane is generally synthesized by a polycondensation reaction but the step of purifying a synthesized polymer is needed as a salt is by-produced by polycondensation. It has recently been disclosed in "Macromolecules, vol. 27, pp. 2360, (1994))" that poly (phenylnanomethylpentasilanylene) 2 is synthesized by the anionic ring-opening polymerization of phenylnanomethyl-cyclopentasilane 1. The ring-opening polyaddition reaction of this cyclic monomer by-produces nothing unlike the above polycondensation reaction and is excellent as a means of synthesizing a high-purity polysilane. This ring-opening addition polymerization is particularly preferred in application fields which require high purity such as electronic materials. However, since the above monomer has the carbon atom of a methyl group (Me) or phenyl group (Ph) bonded to a silicon atom, even when the above polysilane is thermally decomposed polycarbosilane containing a carbon atom is formed, while silicon for semiconductors cannot be obtained.

It is an object of the present invention to provide a novel cyclosilane compound consisting of silicon atoms and hydrogen atoms.

It is another object of the present invention to provide a solution composition suitable for forming a silicon film, particularly an amorphous silicon film or polycrystal silicon film on the surface of a substrate based on the new fact that the above cyclosilane compound of the present invention provides a high-purity and solvent-soluble polysilane by the radical ring-opening addition polymerization of a cyclopentasilane without by-producing a salt.

It is still another object of the present invention to provide a process for forming a silicon film having uniform thickness and a mirror surface on a substrate in a short period of time.

Other object and advantages of the present invention will become apparent from the following description.

According to the present invention, firstly, the above objects and advantages of the present invention are attained by silylcyclopentasilane represented by the following formula (A):

(A)

According to the present invention, secondly, the above objects and advantages of the present invention are attained by a solution composition for forming a silicon film which contains cyclopentasilane represented by the following formula (B) and silylcyclopentasilane represented by the above formula (A):

$$\begin{array}{c} H_2 \\ Si \\ H_2Si \diagup \diagdown SiH_2 \\ | \quad | \\ H_2Si \text{---} SiH_2 \end{array}$$
(B)

According to the present invention, thirdly, the above objects and advantages of the present invention are attained by a process for forming a silicon film on the surface of a substrate, the process comprising the steps of:
(1) preparing the above solution composition for forming a silicon film of the present invention;
(2) coating the surface of a substrate with this solution composition to form a coating film; and
(3) heating this coating film to form a silicon film.

Further, according to the present invention, there is also provided spiro[4.4] nonasilane represented by the following formula (C) and having the function of radically ring-opening polymerizing cyclopentasilane like the silylcyclopentasilane of the present invention:

(C)

DETAILED DESCRIPTION OF THE PREFERRED EMBODIMENT

The present invention will be described in further detail hereinbelow.

The process for synthesizing silylcyclopentasilane of the present invention will be first described.

As for a process for synthesizing the skeleton of silylcyclopentasilane, it is reported in J. Organomet. Chem. vol. 100, pp. 127, (1975) that dodecamethylcyclohexasilane is re-arranged to trimethylsilylnonamethylcyclopentasilane quantitatively by treating it with an aluminum chloride catalyst and that the skeleton of cyclohexasilane is re-arranged to the skeleton of silylcyclopentasilane which is stable thermodynamically. However, all the substituents of the skeleton of silylcyclopentasilane are a methyl group and not hydrogen. It is known that a polysilane having the carbon atom of a methyl group bonded to silicon is converted into a carbosilane containing carbon by a dehydrogenation reaction caused by thermal decomposition and cannot be converted into metallic silicon for use in semiconductors.

There are known methods of converting a phenyl group bonded to a silicon atom into a chlorine atom and a hydrogen atom (for example, Mh. Chem. vol. 106, pp. 503, (1975)), (Z. Anorg. Allg. Chem. vol. 621, pp. 1517, (1995)), (J. Chem. Soc., Chem. Commun., 777, (1984)).

The inventors of the present invention have succeeded in converting all the phenyl group substituents of the skeleton of cyclohexasilane into hydrogen atoms and the skeleton of cyclohexasilane into the skeleton of silylcyclopentasilane at the same time as follows. To convert the phenyl groups bonded to the silicon of dodecaphenylcyclohexasilane into hydrogen atoms, they carry out a treatment with an aluminum chloride catalyst as a Lewis acid to convert the skeleton, hydrogenation by introducing hydrogen chloride gas, and reduction with lithium aluminum hydride. Thus, they have succeeded in the development of silylcyclopentasilane consisting of silicon atoms and hydrogen atoms of the present invention.

They have found that silylcyclopentasilane consisting of silicon atoms and hydrogen atoms of the present invention has the chemical property of converting cyclopentasilane consisting of silicon atoms and hydrogen atoms into a solvent-soluble polysilane by radical ring-opening addition polymerization. The obtained polysilane solution has excellent coatability and is capable of forming on a substrate a satisfactory polysilane coating film which can be converted into a metallic silicon film by a dehydrogenation reaction caused by thermal decomposition or optical decomposition.

The silylcyclopentasilane of the present invention can be used as a radical polymerization initiator for cyclopentasilane. That is, even when only cyclopentasilane is dissolved in a hydrocarbon-based solvent such as toluene and this solution is heated at around the boiling point of the solvent, a polymerization reaction does not proceed. Meanwhile, when cyclopentasilane and a small amount, for example, 1 wt % of silylcyclopentasilane are dissolved in a hydrocarbon-based solvent such as toluene, the polymerization reaction of cyclopentasilane proceeds smoothly. It is presumed that this is due to the mechanism that the silyl group ($SiH_3$) of silylcyclopentasilane is cleaved into radicals and the formed radicals initiate the polymerization of cyclopentasilane.

The solution composition for forming a silicon film of the present invention contains silylcyclopentasilane and cyclopentasilane.

The solution composition of the present intention can be prepared by dissolving these compounds in an appropriate solvent. Any solvent is acceptable if it dissolves cyclopentasilane and silylcyclopentasilane and does not react with a solvent. Preferred examples of the solvent include hydrocarbon-based solvents such as n-heptane, n-octane, decane, toluene, xylene, cymene, durene, indene, dipentene, tetrahydronaphthalene, decahydronaphthalene and cyclohexylbenzene; ether-based solvents such as ethylene glycol dimethyl ether, ethylene glycol diethyl ether, ethylene glycol methyl ethyl ether, diethylene glycol dimethyl ether, diethylene glycol diethyl ether, diethylene glycol methyl ethyl ether and p-dioxane; and aprotic solvents such as propylene carbonate, γ-butyrolactone, N-methyl-2-pyrrolidone, dimethylformamide, dimethylsulfoxide and cyclohexanone. In these, hydrocarbon-based solvents and ether-based solvents are more preferred from the viewpoints of the solubility of a cyclic silicon compound and the stability of the solution, ether-based solvents are much more preferred, and hydrocarbon-based solvents are particularly preferred. These solvents may be used alone or in admixture of two or more.

The solution composition of the present invention can be prepared by making effective use of silylcyclopentasilane by-produced by the synthesis of cyclopentasilane. That is, diphenyldichlorosilane is cyclized by magnesium or metallic lithium contained in tetrahydrofuran to form decaphenylcyclopentasilane and dodecaphenylcyclohexasilane, and a mixture of these is treated in toluene with aluminum chloride, hydrogen chloride gas and then a combination of lithium aluminum hydride and silica gel to form cyclopentasilane from decaphenylcyclopentasilane and skeleton converted silylcyclopentasilane from dodecaphenylcyclohexasilane. A solution of a mixture of silylcyclopentasilane and cyclopentasilane can be used as the solution composition of the present invention.

The solid content of the solution composition of the present invention is preferably 0.01 to 30 wt %, more preferably 0.1 to 20 wt %, particularly preferably 1 to 10 wt % though its appropriate range differs according to the thickness of a silicon film to be formed.

As for the ratio of cyclopentasilane and silylcyclopentasilane, the amount of silylcyclopentasilane is preferably 0.01 to 30 parts by weight, more preferably 0.5 to 20 parts by weight based on 100 parts by weight of cyclopentasilane.

The silicon film forming process of the present invention will be described hereinbelow.

In the step (1), the solution composition of the present invention is prepared as described above, for example. In the next step (2), this solution composition is applied to a substrate to form a coating film. The material, shape and the like of the substrate are not particularly limited but a material which can withstand the heat treatment of the subsequent step is preferred. The substrate on which the coating film is formed is preferably flat. The substrate is made from glass, metal, plastic or ceramic. The glass is selected from quartz glass, borosilicate glass, soda glass and lead glass, the metal is selected from gold, silver, copper, nickel, aluminum, iron and stainless steel, and the plastic is selected from polyimide and polyether sulfone. The shape of the material is not particularly limited and may be plate-like or film-like.

To form a coating film of the solution composition of the present invention, the solution composition can be filtered with a membrane filter made from Teflon or regenerated cellulose to remove solid foreign matter.

To apply the solution composition of the present invention, the coating method is not particularly limited and may be carried on by spin coating, dip coating, curtain coating, roll coating, spray coating or ink jet coating. Coating can be carried out one time or plural times. The preferred thickness of the coating film which changes according to the solid content is preferably 0.01 to 100 μm, more preferably 0.1 to 10 μm after the solvent is removed.

In the final step (3), the coating film is heated. By heating, the solvent contained in the solution composition is volatilized and the silicon compound contained in the coating film is decomposed to form a silicon film. Surprisingly, the formed silicon film has uniform thickness and a mirror surface thanks to silylcyclopentasilane contained in the coating film heated in the step (3). This is because a silicon film having nonuniform thickness is often obtained or a partially broken silicon film is obtained in some cases from a coating film containing no silylcyclopentasilane.

The heating temperature is preferably 300° C. or more, more preferably 400 to 500° C. The heating time is approximately 30 seconds to 30 minutes. The heating atmosphere is preferably an inert atmosphere such as nitrogen, helium or argon atmosphere. It may contain a reducing gas such as hydrogen as required. Not elucidated yet, according to researches conducted by the present inventors, it is believed that the solvent is first volatilized by heating, the radical ring-opening reaction of cyclopentasilane occurs at the same time or after volatilization, part of cyclopentasilane is converted into an oligomer, hydrogen is formed by the thermal decomposition of this oligomer and cyclopentasilane, and a silicon film is formed at the same time. It is also believe that the contained silylcyclopentasilane forms a silyl radical and cyclopentasilanyl radical even when it is deprived of the silyl group.

In the step (3), the coating film may be irradiated with ultraviolet radiation before heating as required. The ultraviolet radiation having dosage of 0.1 to 100 J/cm$^2$ at 365 nm suffices. The light source of ultraviolet radiation may be a low-pressure or high-pressure mercury lamp, heavy hydrogen lamp, argon, krypton or xenon rare gas discharge lamp, YAG laser, argon laser, carbon acid gas laser, or XeF, XeCl, XeBr, KrF, KrCl, ArF or ArCl excimer laser. These light sources generally have an output of 10 to 5,000 W but an output of 100 to 1,000 W suffices.

According to the process of the present invention, a silicon film, particularly an amorphous silicon film can be advantageously formed on the substrate. The thickness of the silicon film can be 0.001 to 10 μm.

The solution composition of the present invention may contain a trace amount of a fluorine-based, silicone-based or nonionic surface tension controlling material as required unless it impairs the object of the present invention. This nonionic surface tension controlling material improves the wettability of the solution for an object to be coated, the leveling properties of a coating film and prevents the formation of bumps on the coating film. The nonionic surfactant is a fluorine-based surfactant having a fluoroalkyl group or perfluoroalkyl group, or polyetheralkyl-based surfactant having an oxyalkyl group. Examples of the fluorine-based surfactant include $C_9F_{19}CONHC_{12}H_{25}$, $C_8F_{17}SO_2NH-(C_2H_4O)_6H$, $C_9F_{17}O$(Pulronic L-35)$C_9F_{17}$, $C_9F_{17}O$ (Pulronic P-84)$C_9F_{17}$ and $C_9F_7O$(Tetronic-704)$(C_9F_{17})_2$ (Pulronic L-35: manufactured by Asahi Denka Kogyo K.K., polyoxypropylene-polyoxyethylene block copolymer having an average molecular weight of 1,900; Pulronic P-84: manufactured by Asahi Denka Kogyo K.K., polyoxypropylene-polyoxyethylene block copolymer having an average molecular weight of 4,200; Tetronic-704: manufactured by Asahi Denka Kogyo K.K., N,N,N ,N -tetrakis (polyoxypropylene-polyoxyethylene block copolymer) having an average molecular weight of 5,000). Commercially available products of the fluorine-based surfactant include F Top EF301, EF303 and EF352 (of Shin Akita Kasei Co., Ltd.), Megafac F171 and F173 (of Dainippon Ink and Chemicals, Inc.), Asahi Guard AG710 (of Asahi Glass Co., Ltd.), Florade FC-170C, FC430 and FC431 (Sumitomo 3M, Ltd.), Surflon S-382, SC101, SC102, SC103, SC104, SC105 and SC106 (of Asahi Glass Co., Ltd.), BM-1000 and 1100 (of B.M-Chemie Co., Ltd.) and Schsego-Fluor (of Schwegmann Co., Ltd.). Examples of the polyetheralkyl-based surfactant include polyoxyethylene-alkyl ethers, polyoxyethyleneallyl ethers, polyoxyethylene-alkyl phenol ethers, polyoxyethylene fatty acid esters, sorbitan fatty acid esters, polyoxyethylene sorbitan fatty acid esters and oxyethylene oxypropylene block polymers. Commercially available products of the polyetheralkyl-based surfactant include Emulgen 105, 430, 810 and 920, Leodor SP-40S and TW-L120, Emanol 3199 and 4110, Excel P-40S, Bridge 30, 52, 72 and 92, Arassel 20, Emasol 320, Tween 20 and 60, and Merge 45 (of Kao Corporation) and Noniball 55 (of Sanyo Chemical Industries, Ltd.). Nonionic surfactants other than the above include polyoxyethylene fatty acid esters, polyoxyethylene sorbitan fatty acid esters and polyalkylene oxide block copolymers and commercially available products thereof include Chemistat 2500 (of Sanyo Chemical Industries, Ltd.), SN-EX9228 (of Sun Nopco Co., Ltd.) and Nonale 530 (of Toho Chemical Ind., Co., Ltd.).

The amorphous silicon film formed by the present invention is used in various electronic devices such as solar cells, photosensors, thin film transistors, photosensitive drums and protective films.

Finally, according to the present invention, there is also provided spiro[4.4] nonasilane which has the function of radically ring-opening polymerizing cyclopentasilane like the silylcyclopentasilane of the present invention.

The spiro[4.4] nonasilane of the present invention can be synthesized by known methods in which a phenyl group bonded to the silicon atom of hexadecaphenylspiro[4.4] nonasilane is converted into a chlorine atom and then converted into a hydrogen atom (for example, Mh. Chem. vol. 106, pp. 503, (1975)), (Z. Anorg. Allg. Chem. vol. 621, pp. 1517, (1995)), (J. Chem. Soc., Chem. Commun., 777, (1984)).

For example, hexadecaphenylspiro[4.4] nonasilane is chlorinated by introducing hydrogen chloride gas in the presence of a Lewis acid catalyst such as aluminum chloride and then hydrogenated with lithium aluminum hydride to convert all the phenyl substituents of hexadecaphenylspiro [4.4] nonasilane into hydrogen atoms to produce spiro [ 4.4] nonasilane consisting of silicon atoms and hydrogen atoms.

The chlorination reaction can be carried out at a temperature of 0 to 80° C. for 1 to 12 hours. The Lewis acid catalyst may be used in an amount of 0.1 to 20 wt % based on hexadecaphenylspiro[4.4] nonasilane. An organic solvent such as toluene is used as the reaction solvent.

The reduction reaction is carried out at a temperature of 0 to 50° C. for 1 to 24 hours.

The hexadecaphenylspiro[4.4] nonasilane as a raw material is obtained by the dehalogenation and condensation of diphenyldichlorosilane and tetrachlorosilane in the presence of metallic lithium.

The silylcyclopentasilane of the present invention may be used as a radical polymerization initiator for cyclopentasilane and also a radical initiator for a vinyl monomer. In this case, a vinyl polymer having a silicon atom at the terminal of a polymer molecule is obtained, thereby making it possible to derive a block or random copolymer of the vinyl polymer and a silicon-based polymer.

Examples of the above vinyl monomer include aromatic vinyl compounds such as styrene, α-methylstyrene, o-vinyltoluene, m-vinyltoluene, p-vinyltoluene, p-chlorostyene, o-methoxystyrene, m-methoxystyrene and p-methoxystyrene; acrylates and methacrylates such as methyl acrylate, methyl methacrylate, ethyl acrylate, ethyl methacrylate, n-propyl acrylate, n-propyl methacrylate, i-propyl acrylate, i-propyl methacrylate, n-butyl acrylate, n-butyl methacrylate, i-butyl acrylate, i-butyl methacrylate, sec-butyl acrylate, sec-butyl methacrylate, t-butyl acrylate, t-butyl methacrylate, 2-hydroxyethyl acrylate and 2-hydroxyethyl methacrylate; and aliphatic conjugated dienes such as 1,3-butadiene, isoprene and chloroprene.

The following examples are provided for the purpose of further illustrating the present invention but are in no way to be taken as limiting.

EXAMPLES

Example 1

(1) The inside of a 2-liter four-necked flask equipped with a thermometer, condenser, dropping funnel and stirrer was substituted with argon gas, and 1.5 liters of dried tetrahydrofuran and 27.4 g of metallic lithium were charged into the flask and bubbled with argon gas. To this suspension was added 500 g of diphenyldichlorosilane by the dropping funnel while it was stirred under cooling with ice. After a reaction was continued until metallic lithium completely disappeared, the reaction mixture was poured into iced water to precipitate the reaction product. This precipitate was separated by filtration and washed well in water and then cyclohexane. Further, this crude product was recrystallized with ethyl acetate to obtain 216 g of dodecaphenylcyclohexasilane. The structure of this product was confirmed by TOF-MS, NMR and IR. Thereafter, 100 g of this dodecaphenylcyclohexasilane and 1,000 ml of toluene were charged into a 2-liter flask, 50 g of aluminum chloride was added and stirred at room temperature in an argon gas atmosphere for 5 hours and then hydrogen chloride gas was introduced until the phenyl group disappeared. The product obtained from this reaction was found to be dodecachlorocyclohexasilane by its $^{29}$Si-NMR and IR spectra. Thereafter, the above reaction mixture was gradually added to a solution of 42 g of lithium aluminum hydride suspended in 500 ml of diethyl ether and stirred at room temperature for 12 hours. This reaction mixture was filtered to obtain an achromatic and transparent silylcyclopentasilane solution.

Figure 1:
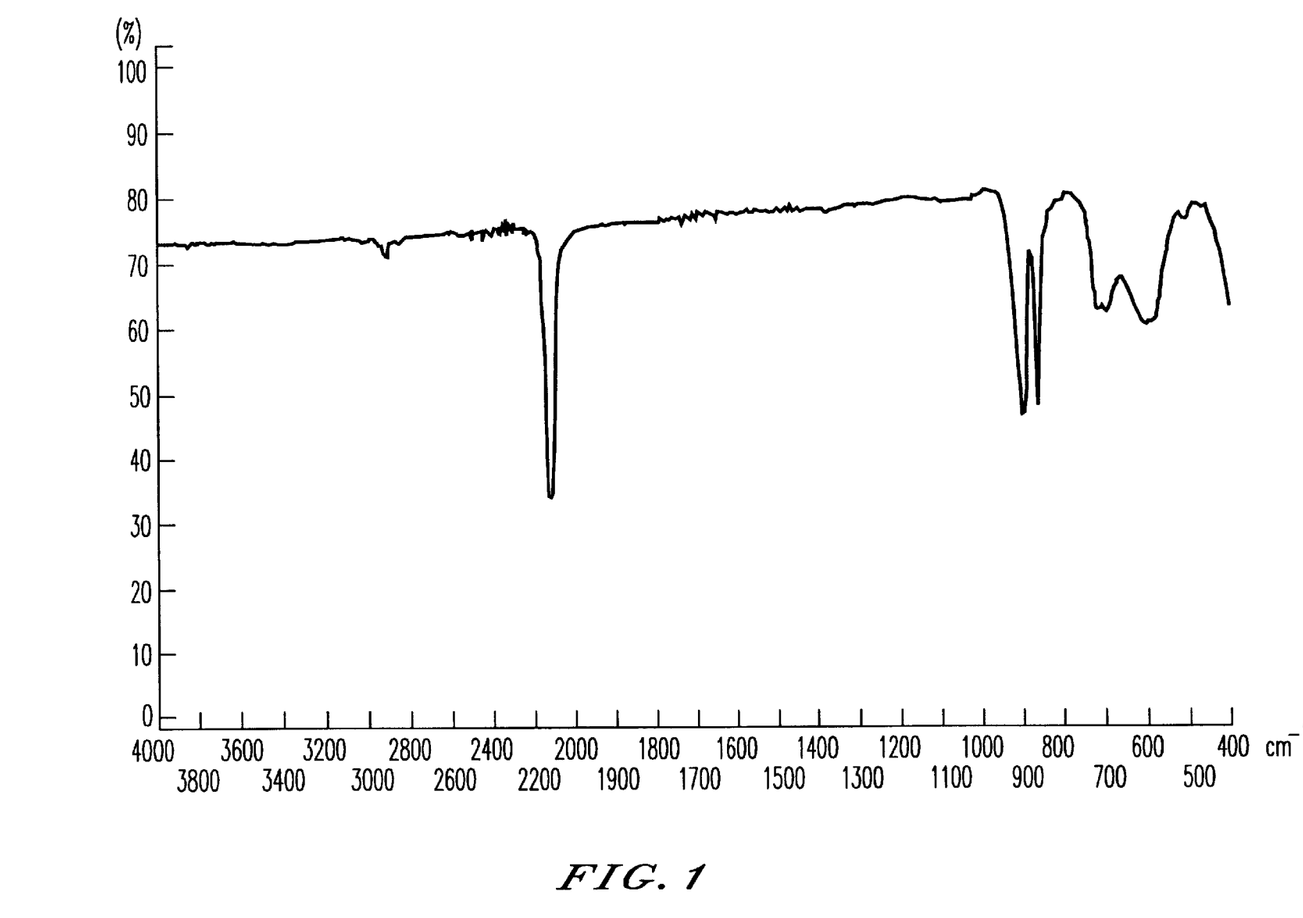
FIG. 1 is a diagram showing the infrared absorption spectrum of silylcyclopentasilane.
Figure 2:
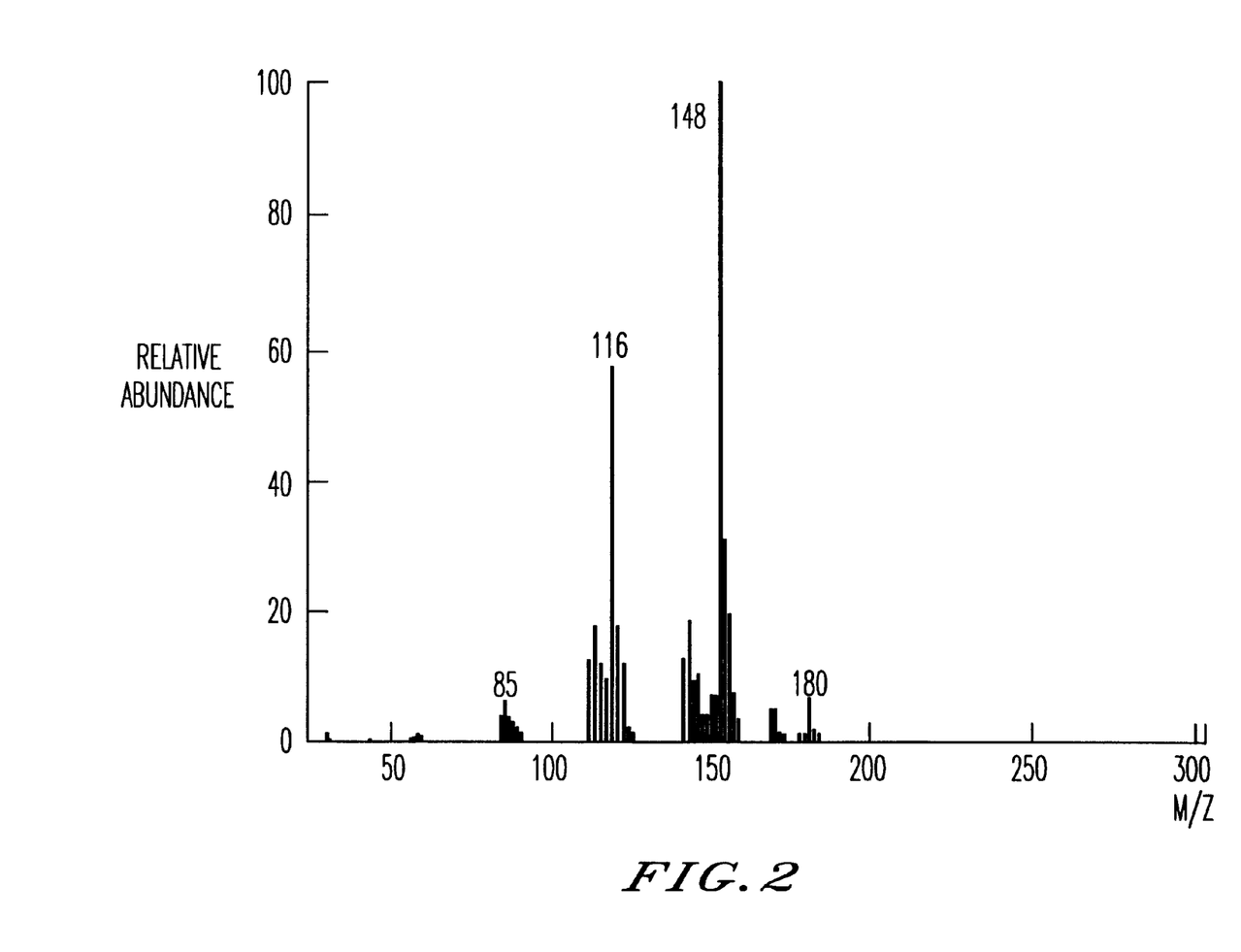
FIG. 2 is a diagram showing the mass spectrum of silylcyclopentasilane.

(2) The obtained silylcyclopentasilane was oily at room temperature and its infrared absorption spectrum is shown in FIG. 1. This silylcyclopentasilane consists of silicon atoms and hydrogen atoms, its infrared spectrum is relatively simple, a sharp peak attributed to the stretching vibration of a silicon-hydrogen bond is observed at 2,125 cm$^{-1}$ and peaks attributed to the stretching vibration of a silicon-silicon bond are observed at 985 cm$^{-1}$ and 863 cm$^{-1}$. FIG. 2 shows the mass spectrum of the silylcyclopentasilane. Since a molecular ion peak is observed at an m/e of 180, the molecular weight of the substance is 180. A strong peak detected at an m/e of 148 is attributed to a fragment formed by the elimination of one monosilane (SiH$_4$) from the molecule of silylcyclopentasilane and a peak at an m/e of 116 is attributed to a fragment formed by the elimination of two monosilanes from the molecule of silylcyclopentasilane.

As for the chemical properties of silylcyclopentasilane, silylcyclopentasilane can be easily dissolved in an ordinary organic solvent such as a hydrocarbon solvent exemplified by benzene, toluene, xylene, hexane, cyclohexane, indane and decahydronaphthalene, ether-based solvent exemplified by diethyl ether, tetrahydrofuran, monoglyme and diglyme, or ketone-based solvent exemplified by acetone, methyl ethyl ketone, methyl isobutyl ketone or methyl amyl ketone in any ratio.

Silylcyclopentasilane is an achromatic and transparent oily substance at room temperature as described above and extremely stable in an inert atmosphere such as argon or nitrogen. However, when it is left in the air, it is gradually oxidized and readily converted into a siloxane structure. When silylcyclopentasilane is heated at 300° C. or more in an inert atmosphere, a dehydrogenation reaction occurs to convert it into amorphous metallic silicon. Further, this silylcyclopentasilane generates a radical by heating at approximately 100° C. to radically ring-opening polymerize the above cyclopentasilane to convert it into a solvent-soluble polysilane. Further, it can polymerize a radical polymerizable monomer such as a vinyl compound exemplified by a general acrylic compound.

Figures 5, 6:
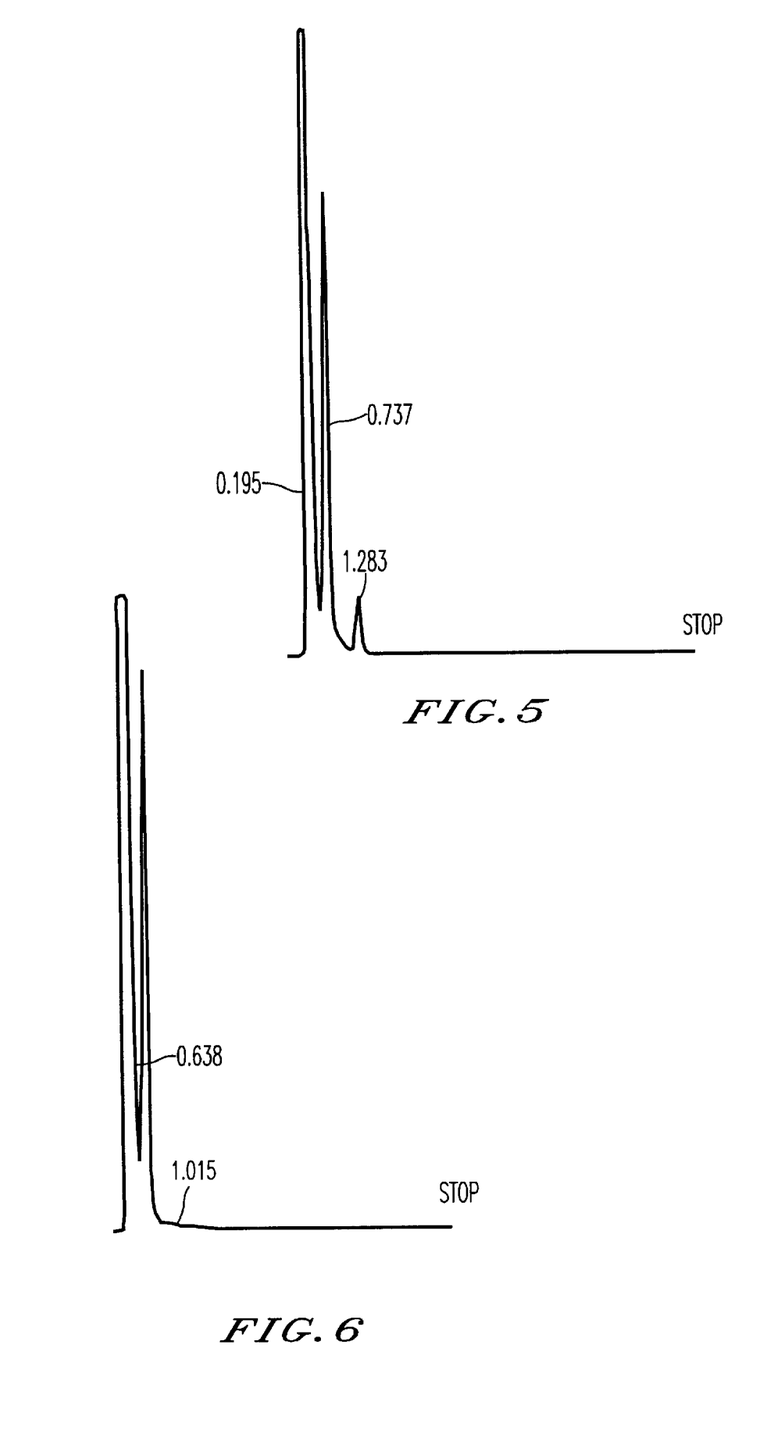
FIG. 5 is a diagram showing the gas chromatogram (GLC) of a toluene solution of a mixture of cyclopentasilane and silylcyclopentasilane (weight ratio of 9/1)
FIG. 6 is a diagram showing the gas chromatogram (GLC) of a toluene solution of cyclopentasilane.

The gas chromatography of silylcyclopentasilane and cyclopentasilane is obtained by using Chromosorb W (60 to 80 mesh) as a carrier, silicone OV-17 (5%) as a liquid phase and helium gas at 120° C. (see FIG. 5 and FIG. 6).

Example 2

The inside of a 2-liter three-necked flask equipped with a thermometer, condenser and stirrer was substituted with argon gas, and 1.5 liters of dried tetrahydrofuran and 3.8 g of metallic lithium were charged into the flask and bubbled with argon gas. To this suspension was added 100 g of octaphenylcyclobutasilane synthesized by the method of Hengge et al. (J. Organomet. Chem., vol. 212, pp. 155, (1981)) while it was stirred at room temperature for 5 hours to ring-open octaphenylcyclobutasilane so as to form a dianion. 50 g of triphenylsilylphenyldichlorosilane was added and reacted while this dark brown dianion solution was stirred at room temperature. The reaction mixture was poured into 2 liters of iced water to precipitate the product. The obtained product was separated by filtration, washed in water and then cyclohexane and dried under reduced pressure to obtain 108 g of triphenylsilylnonaphenylcyclopentasilane. Further, 50 g of the obtained triphenylsilyl-nonaphenylcyclopentasilane was dissolved in 500 ml of toluene and 5 g of anhydrous alminum chloride was added to react hydrogen chloride gas with triphenylsilylnonaphenylcyclopentasilane until a phenyl group disappeared. Thereafter, this reaction product solution was added to a solution containing 20 g of lithium aluminum hydride suspended in 100 ml of diethyl ether and stirred at room temperature for 12 hours. The reaction mixture was treated with a silica gel and concentrated to obtain an achromatic and transparent oily substance. The IR and MS spectra of this substance was identified with those of the product of above Example 1.

Reference Example 1

Figure 3:
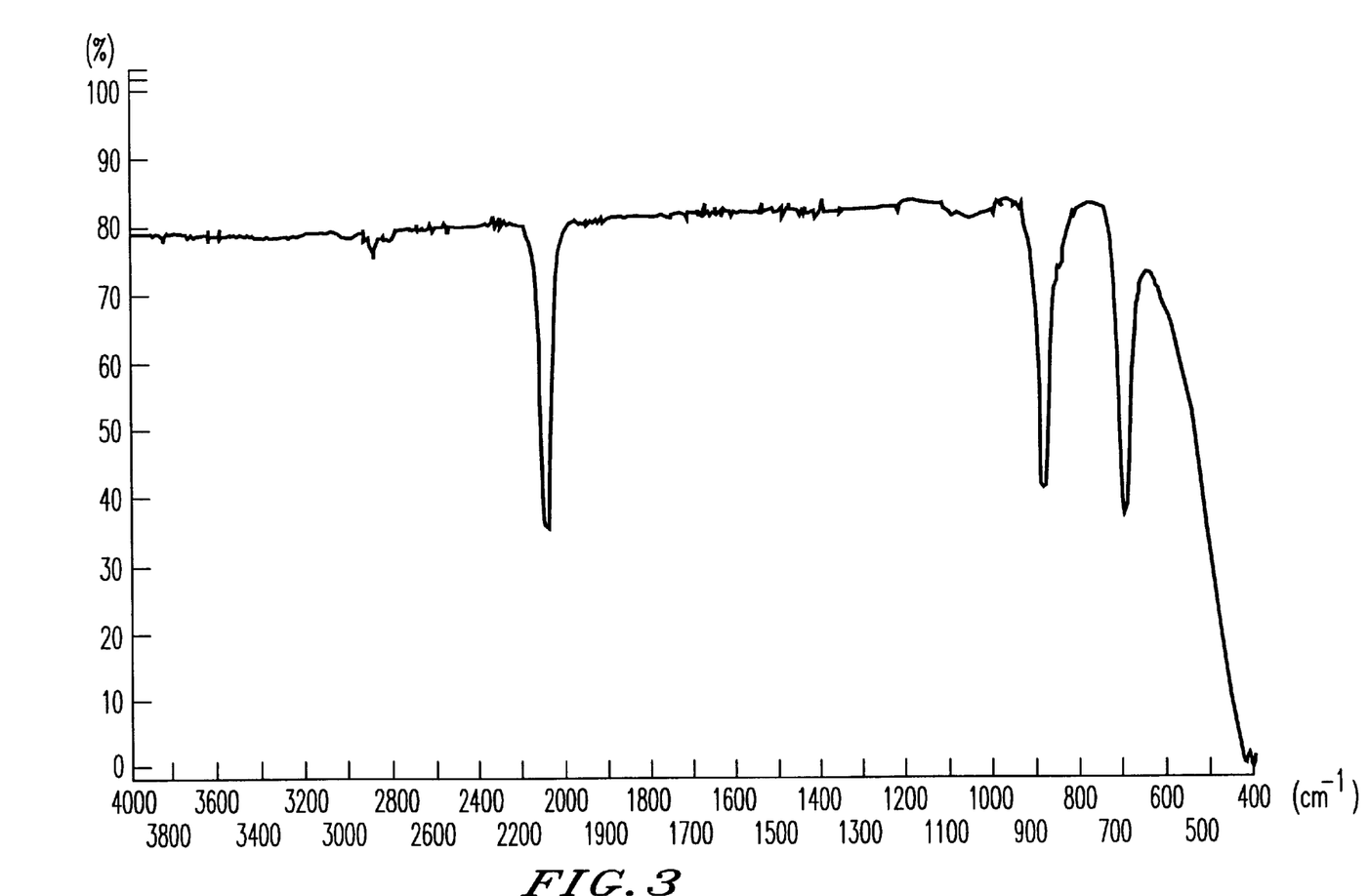
FIG. 3 is a diagram showing the infrared absorption spectrum of cyclopentasilane.
Figure 4:
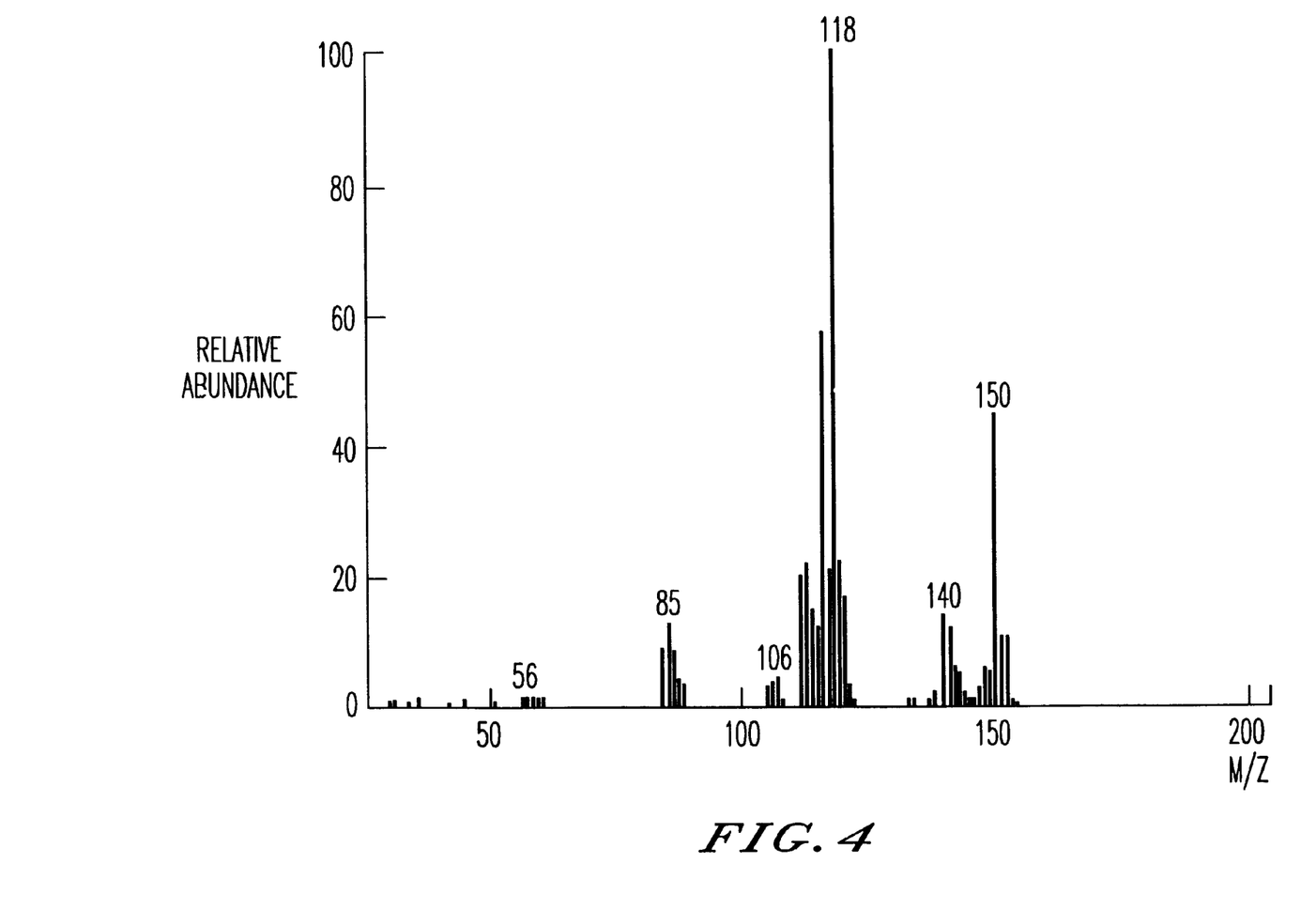
FIG. 4 is a diagram showing the mass spectrum of cyclopentasilane.

50 g of decaphenylcyclopentasilane and 500 ml of toluene were charged into a 2-liter four-necked flask equipped with a thermometer, condenser and stirrer. 5 g of anhydrous aluminum chloride was added to this reaction solution and further hydrogen chloride gas was reacted with decaphenyl-cyclopentasilane at room temperature for 5 hours. The disappearance of a phenyl group was confirmed by NMR of the reaction system. Thereafter, this reaction mixture was added to a solution containing 20 g of lithium aluminum hydride prepared separately and suspended in 100 ml of diethyl ether and stirred at room temperature for 12 hours. The reaction mixture was treated with a silica gel and concentrated to obtain achromatic and transparent oily cyclopentasilane. The IR spectrum of this substance is shown in FIG. 3 and the MS spectrum thereof is shown in FIG. 4.

Example 3

(1) The inside of a 3-liter four-necked flask equipped with a thermometer, cooling condenser, dropping funnel and stirrer was substituted with argon gas, and 1 liter of dried tetrahydrofuran and 18.3 g of metallic lithium were charged into the flask and bubbled with argon gas. To this suspension solution was added 333 g of diphenyldichlorosilane by the dropping funnel while it was stirred at 0° C. and stirring was further continued at room temperature for 12 hours until the metallic lithium completely disappeared after end of addition. The reaction mixture was poured into 5 liters of iced water to precipitate the reaction product. This precipitate was separated by filtration, washed well in water and then cyclohexane and vacuum dried to obtain 140 g of a white solid The IR, $^1$H-NMR and $^{29}$Si-NMR spectra of the white solid showed that it was a mixture of two components (to be referred to as silicon compound mixture A hereinafter). When this silicon compound mixture A was separated by high-speed liquid chromatography, the ratio of the main product to the by-product was 8:1. When the IR, $^1$H-NMR, $^{29}$Si- NMR and TOF-MS spectra of the main product and the by-product were further measured, it was confirmed that the main product was decaphenylcyclopentasilane (to be referred to as silicon compound B hereinafter) and the by-product was dodecaphenylcyclohexasilane (to be referred to as silicon compound C hereinafter).

(2) 50 g of the above silicon compound mixture A and 500 ml of dried toluene were charged into a 1-liter flask, 2 g of aluminum chloride was added, and hydrogen chloride was introduced at room temperature to continue a reaction in an argon atmosphere for 5 hours. 20 g of lithium aluminum hydride and 200 ml of diethyl ether were charged into a 2-liter flask separately, and the above reaction mixture was added at 0° C. in an argon atmosphere under agitation, stirred at the same temperature for 1 hour and further kept stirred at room temperature for 12 hours. An aluminum compound was removed from the reaction mixture and the solvent was distilled off to obtain 5 g of a viscous oily product. It was found from its IR, $^1$H-NMR, $^{29}$Si-NMR and GC-MS spectra that this product was a mixture (to be referred to as silicon compound mixture F hereinafter) of cyclopentasilane (to be referred to as silicon compound D hereinafter) and silylcyclopentasilane (to be referred to as silicon compound E hereinafter) in a ratio of 8:1.

(3) When 85 g of the silicon compound mixture A was recrystallized with 4 liters of ethyl acetate, 55 g of the pure silicon compound B was obtained. When 50 g of the thus obtained silicon compound B was subjected to the above step (2), 5 g of the pure silicon compound D was obtained. It was confirmed by gas chromatography that this compound had a purity of 99% or more.

Example 4

Figure 7:
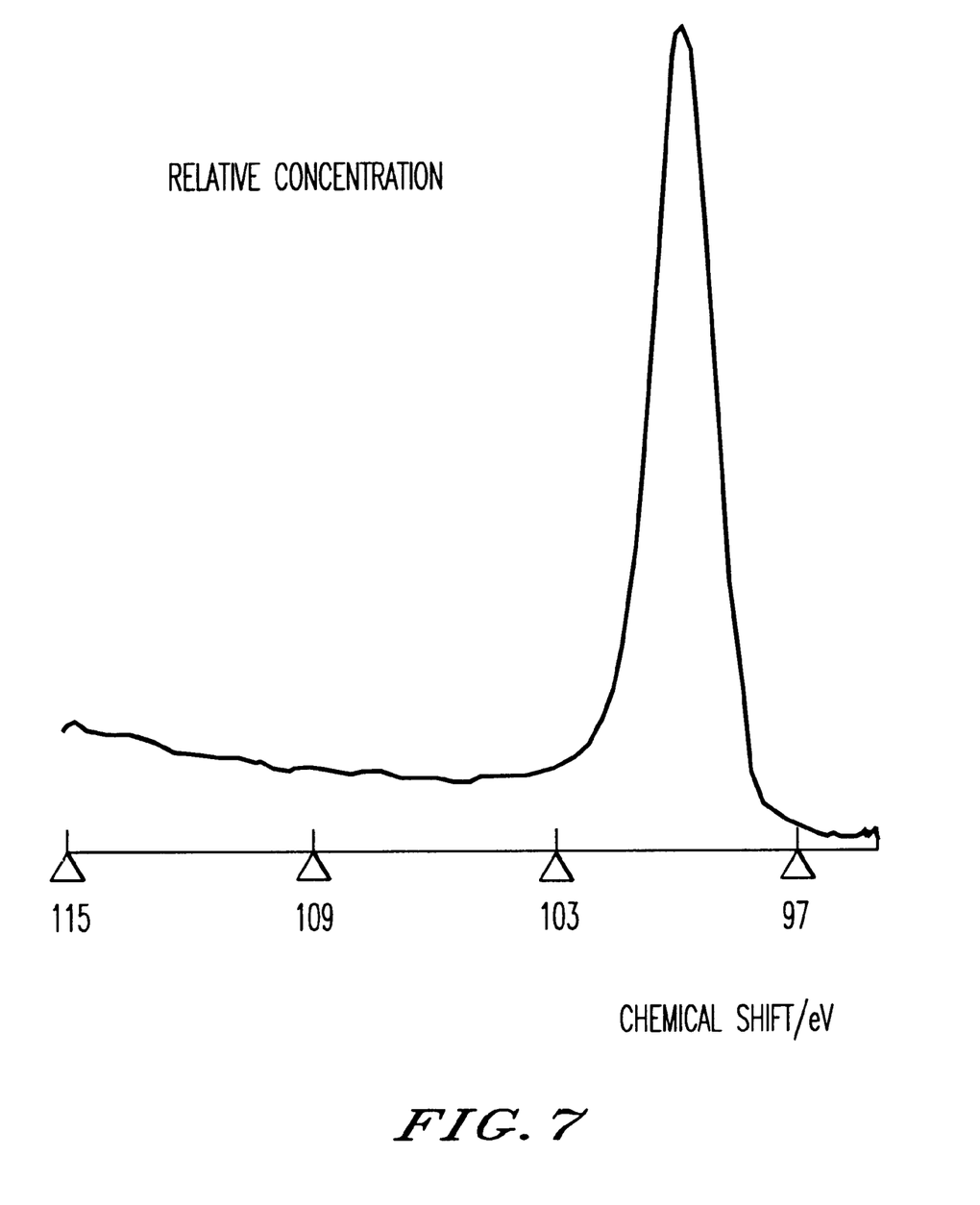
FIG. 7 is a diagram showing the ESCA spectrum of the silicon film obtained in Example 4.

5 g of the silicon compound mixture F obtained in (2) of Example 3 was dissolved in 95 g of toluene in an argon atmosphere to prepare a solution. This solution was spin coated on a quartz substrate in an argon atmosphere to form a film of the silicon compound mixture F. When this coated substrate was heated at 500° C. in an argon atmosphere for 5 minutes, a silicon film remained on the substrate. It was found from its Raman scattering spectrum that this silicon film was 100% amorphous. When this amorphous silicon was irradiated with light from an XeCl excimer laser (308 nm), silicon was polycrystallized to a crystallinity of 75%. When the 2P orbital energy of a silicon atom was measured from the ESCA spectrum of the polycrystallized silicon film, it was found to be 99.0 eV which verified that it was silicon. FIG. 7 shows the ESCA spectrum of the silicon film.

Comparative Example 2

5 g of the silicon compound D obtained in (3) of Example 3 was dissolved in 95 g of toluene in an argon atmosphere to prepare a solution. This solution was spin coated on a quartz substrate in an argon atmosphere but a uniform film could not be obtained due to the cissing of the solution.

Example 5

5 g of the silicon compound mixture F obtained in (2) of Example 3 was dissolved in 95 g of toluene in an argon atmosphere to prepare a solution. This solution was spin coated on a quartz substrate in an argon atmosphere to form a film of the silicon compound mixture F. When this coated substrate was irradiated with UV in an argon atmosphere and heated at 500° C. for 5 minutes, a silicon film remained on the substrate. It was found from its Raman scattering spectrum that this silicon film was 100% amorphous. When this amorphous silicon was irradiated with light from an XeCl excimer laser (308 nm), silicon was polycrystallized to a crystallinity of 75%. When the 2P orbital energy of a silicon atom was measured from the ESCA spectrum of the polycrystallized silicon film, it was found to be 99.0 eV which verified that it was silicon.

Example 6

Figure 8:
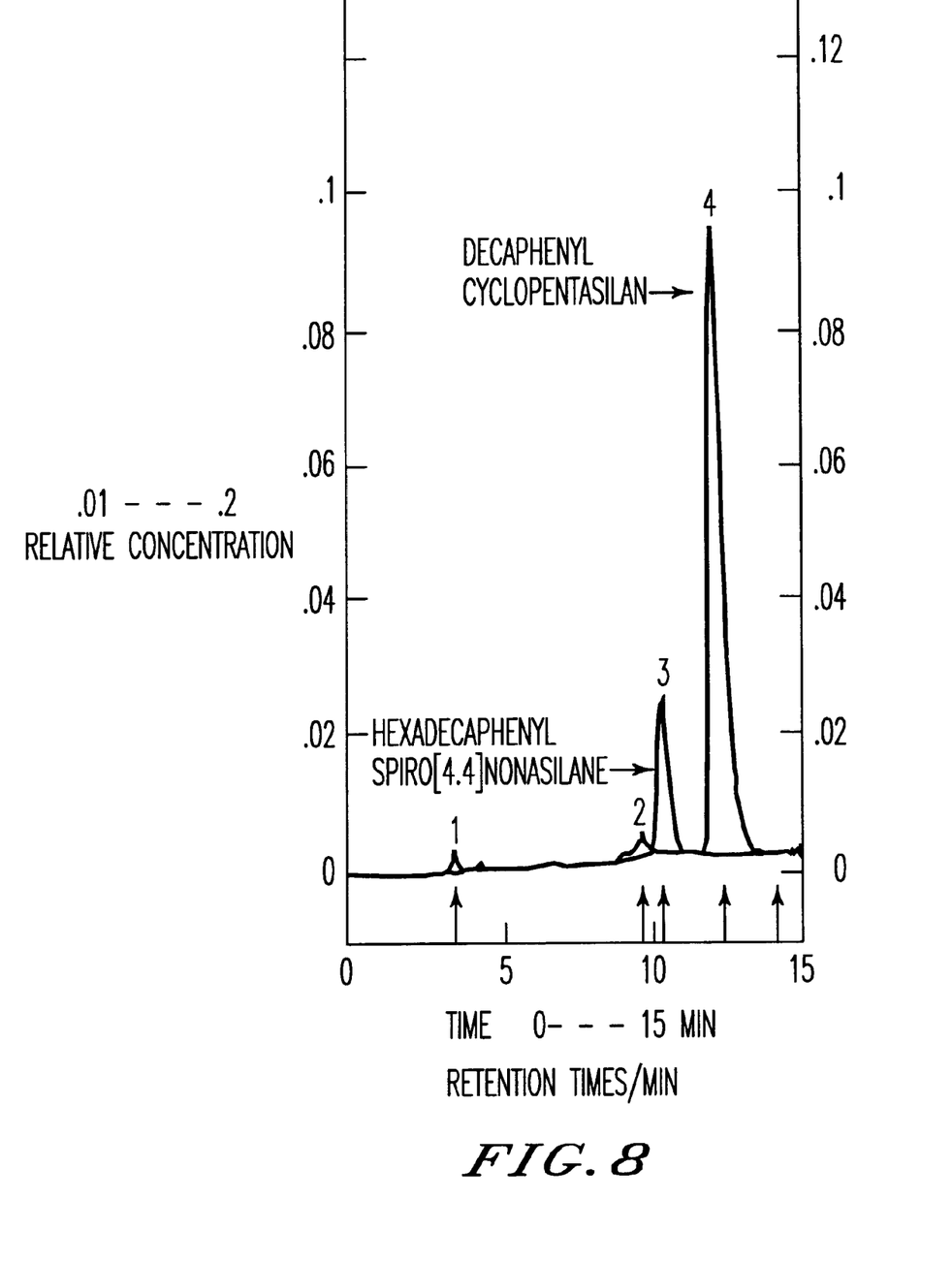
FIG. 8 is a diagram showing the high-speed liquid chromatogram of the mixture obtained in Example 6(1).

(1) The inside of a 3-liter four-necked flask equipped with a thermometer, cooling condenser, dropping funnel and stirrer was substituted with argon gas, and 1 liter of dried tetrahydrofuran and 20.3 g of metallic lithium were charged into the flask and bubbled with argon gas. To this suspension solution was added a mixture of 296 g of diphenyldichlorosilane and 24.8 g of tetrachlorosilane by the dropping funnel while it was stirred at 0° C. After the end of addition, stirring was further continued at 25° C. for 12 hours until the metallic lithium completely disappeared. The reaction mixture was poured into 5 liters of iced water to precipitate the reaction product. This precipitate was separated by filtration, washed well in water and then cyclohexane and vacuum dried to obtain 180 g of a white solid. The IR, $^1$H-NMR and $^{29}$Si-NMR spectra of this white solid showed that it was a mixture of two components. When this mixture was separated by high-speed liquid chromatography, it was found that the ratio of the main product to the by-product was 9:1. When the IR, $^1$H-NMR, $^{29}$Si-NMR and TOF-MS spectra of these products were further measured, it was confirmed that the main product was decaphenylcyclopentasilane and the by-product was hexadecaphenylspiro[4.4] nonasilane. FIG. 8 shows the high-speed liquid chromatograph of the above mixture.

(2) 50 g of the above mixture of decaphenylcyclopentasilane and hexadecaphenylspiro[4.4] nonasilane obtained in (1) above (in a ratio of 9:1) and 500 ml of dried toluene were charged into a 1-liter flask, 2 g of aluminum chloride was added, and hydrogen chloride was introduced at 25° C. to continue a reaction in an argon atmosphere for 5 hours. 20 g of lithium aluminum hydride and 200 ml of diethyl ether were charged into a 2-liter flask separately and the above reaction mixture was added at 0° C. in an argon atmosphere under agitation, stirred at the same temperature for 1 hour and further kept stirred at 25° C. for 12 hours. An aluminum compound was removed from the reaction mixture and the solvent was distilled off to obtain 5 g of a viscous oily product. It was found from its IR, $^1$H-NMR, $^{29}$Si-NMR and GC-MS spectra that this product was a mixture of cyclopentasilane and spiro[4.4] nonasilane in a ratio of 9:1.

What is claimed is:

1. A process for forming a silicon film on the surface of a substrate comprising:

(1) coating the surface of the substrate with a composition comprising cyclopentasilane represented by the following formula (B):

(B)

and silylcyolopentasilane represented by the following formula (A):

to form a coating film; and (2) heating the coating film to form a silicon film.

2. The process according to claim 1, wherein the silicon film is an amorphous silicon film.

3. The process according to claim 1, wherein the silicon film is a polycrystal silicon film.

4. The process according to claim 1, wherein the silicon film has a uniformn thickness.

5. The process according to claim 1, wherein the silicon film has a mirror surface.

6. The process according to claim 1, wherein the solid content of said solution is 0.01 to 30 wt %.

7. The process according to claim 1, wherein the solid content of said solution is 0.1 to 20 wt %.

8. The process according to claim 1, wherein the solid content of said solution is 1 to 10 wt %.

9. The process according to claim 1, wherein the amount of silylcyclopentasilane is 0.01 to 30 parts by weight based on 100 parts by weight of cyclopentasilane.

10. The process according to claim 1, wherein the amount of silylcyclopentasilane is 0.5 to 20 parts by weight based on 100 parts by weight of cyclopentasilane.

11. The process according to claim 1, wherein the substrate is made from glass, metal, plastic or ceramic.

12. The method according to claim 11, wherein the glass is quartz glass, borosilicate glass, soda glass or lead glass.

13. The method according to claim 11, wherein the metal is gold, silver, copper, nickel, aluminum, iron or stainless steel.

14. The method according to claim 11, wherein the plastic is polyimide or polyether sulfone.

15. The method according to claim 1, wherein the coating is done by spin coating, dip coating, curtain coating, roll coating, spray coating or ink jet coating.

16. The method according to claim 1, wherein the coating film has a thickness of 0.01 to 100 $\mu$m.

17. The method according to claim 1, wherein the coating film has a thickness of 0.1 to 10 $\mu$m.

18. The method according to claim 1, wherein the heating temperature is 300° C. or more.

19. The method according to claim 1, wherein the heating temperature is 400° C. or more.

20. The method according to claim 18, wherein the heating time is 30 seconds to 30 minutes.

21. The method according to claim 1, wherein the coating film is irradiated with ultraviolet radiation before heating.

22. The method according to claim 21, wherein said ultraviolet radiation has a dosage of 0.1 to 100 J/cm$^2$ at 365 nm.

23. The method according to claim 1, wherein the solvent composition contains a trace amount of a fluorine-based silicone-based or non-ionic surface controlling material.

24. Spiro[4.4]nonasilane represented by the following formula (C):

(C)

* * * * *

UNITED STATES PATENT AND TRADEMARK OFFICE
CERTIFICATE OF CORRECTION

PATENT NO.    : 6,503,570 B2
DATED         : January 7, 2003
INVENTOR(S)   : Matsuki et al.

It is certified that error appears in the above-identified patent and that said Letters Patent is hereby corrected as shown below:

<u>Title page,</u>
Item [73], Assignee, "JRS Corporation, Tokyo (JP)" should read
-- JSR Corporation, Tokyo (JP) --.

Signed and Sealed this

Twenty-second Day of July, 2003

JAMES E. ROGAN
*Director of the United States Patent and Trademark Office*